(12) United States Patent
Hattori et al.

(10) Patent No.: US 6,940,527 B2
(45) Date of Patent: Sep. 6, 2005

(54) INSPECTION STATUS DISPLAY METHOD

(75) Inventors: Shinichi Hattori, Tokyo (JP); Tohru Ida, Tokyo (JP)

(73) Assignee: Nippon Avionics Co., Ltd., Tokyo (JP)

( * ) Notice: Subject to any disclaimer, the term of this patent is extended or adjusted under 35 U.S.C. 154(b) by 84 days.

(21) Appl. No.: 10/387,681

(22) Filed: Mar. 13, 2003

(65) Prior Publication Data

US 2004/0098156 A1 May 20, 2004

(30) Foreign Application Priority Data

Nov. 15, 2002 (JP) ........................................ 2002-331707

(51) Int. Cl.[7] .......................... G09G 5/00; G06F 19/00; G06F 17/50; G06K 9/00
(52) U.S. Cl. ........................ 345/629; 700/121; 382/144; 716/21
(58) Field of Search ...................... 716/21, 19; 700/121; 382/144; 345/629

(56) References Cited

U.S. PATENT DOCUMENTS 4,586,822 A * 5/1986 Tanimoto ..................... 356/394
5,027,417 A * 6/1991 Kitakado et al. ............ 382/148
5,774,573 A * 6/1998 Caspi et al. ................. 382/141
6,757,645 B2 * 6/2004 Chang et al. ................. 703/13

FOREIGN PATENT DOCUMENTS

| JP | 62-047504 | 3/1987 |
| JP | 05-332948 | 12/1993 |
| JP | 06-258242 | 9/1994 |
| JP | 09-264856 | 10/1997 |
| JP | 10-141932 | 5/1998 |
| JP | 2002-243657 | 8/2002 |

* cited by examiner

Primary Examiner—Stacy A. Whitmore
Assistant Examiner—Sun James Lin
(74) Attorney, Agent, or Firm—Blakely Sokoloff Taylor & Zafman

(57) ABSTRACT

An object of this invention is to confirm the content of a defect in real time. A defect image, corresponding master pattern image, failure designation button, nondefective designation button, dust designation button, piece number, piece coordinates, and the type of defect are displayed within a defect image region in an inspection status display window. When the nondefective designation button or dust designation button is selected, the inspecting apparatus recognizes that a defect corresponding to the selected button is negligible, and changes the inspection result of this defect from the defect to a nondefective.

12 Claims, 5 Drawing Sheets

INSPECTION STATUS DISPLAY METHOD

BACKGROUND OF THE INVENTION

The present invention relates to an inspecting apparatus which senses an inspection work by a camera and automatically inspects the inspection work and, more particularly, to an inspection status display method of displaying the inspection status of an inspection work.

PGA (Pin Grid Array) has conventionally been known as a packaging technique which meets demands for a larger number of IC or LSI pins. In PGA, a ceramic board is used as a package base for mounting a chip, and wires are laid out to lead line extraction positions. The manufacture of this ceramic board uses a green sheet prepared by kneading alumina power with a liquid binder and shaping the resultant material into a sheet. A past containing a refractory metal is screen-printed on the green sheet. A necessary number of sheets are stacked and baked, performing so-called simultaneous baking of baking the green sheet and metalizing the paste.

A pattern on such a green sheet is inspected by the human eye using a microscope after pattern formation. Visual inspection of a fine pattern requires a skill and overuses the eye. From this, there is proposed a pattern inspecting apparatus which sense a pattern formed on a green sheet or the like by a TV camera and automatically checks the pattern.

FIGS. 5 and 6 explain a conventional inspecting method of detecting disconnection. A master pattern formed by sensing a pattern to be measured that is determined as a nondefective is registered as a set of straight lines representing pattern edges. The pattern to be measured is input as a set of edge data (edge coordinates) representing pattern edges extracted from a gray-scale image obtained by sensing a pattern. Extracted edge data n1, n2, n3, . . . of the pattern to be measured and the straight lines of the master data are made to correspond to each other. For this correspondence, bisectors A2', A3', . . . which bisect angles defined by consecutive straight lines A1 and A2, A2 and A3, . . . of the master pattern are obtained, as shown in FIG. 5.

The bisectors A2', A3', . . . divide the peripheries of the straight lines A1, A2, A3, . . . into regions belonging to the respective straight lines. The edge data n1, n2, n3, . . . of the pattern to be measured that exist in respective regions are made to correspond to the straight lines A1, A2, A3, . . . of the master pattern to which the respective regions belong. For example, in FIG. 5, the edge data n1 to n3 are made to correspond to the straight line A1, whereas the edge data n4 to n6 are made to correspond to the straight line A2.

After that, the edge data of the pattern to be measured and the master pattern are compared to inspect whether the pattern to be measured is disconnected.

This inspection is realized by labeling processing of tracking the coupled edge data n1 to n9 of the pattern to be measured and thus tracking the pattern edge. At this time, edge data are not coupled at a disconnected portion owing to disconnection at the end of the pattern to be measured. Edge data corresponding to the straight lines A3 to A5 of the master pattern do not exist. As a result, disconnection of the pattern to be measured can be detected.

FIG. 7 explains a conventional inspecting method of detecting a short circuit. Coupled edge data of a pattern to be measured are tracked in an inspection region 20 having a predetermined size extracted from a master pattern and the pattern to be measured. Edge data of the pattern to be measured are sequentially labeled as n1 to n18. However, edge data n8 and n17 are not registered in a master pattern Ma formed from two facing straight lines representing pattern edges and a master pattern Mb similarly formed from two facing straight lines. In this manner, the short circuit of the pattern to be measured can be detected (see, e.g., Japanese Patent Laid-Open No. 6-273132; to be referred to as reference 1 hereinafter).

FIG. 8 explains a conventional inspecting method of detecting an omission or projection. A perpendicular to a central line L is drawn, and the length between the intersection points of the perpendicular and straight lines A1 and A2 representing master pattern edges is obtained in advance as a master pattern width W0. In actual inspection, a perpendicular is drawn from edge data n of a pattern to be measured to the central line L of the master pattern, and the distance between facing edge data is obtained. This distance is a width W of the pattern to be measured. The width W is compared with the master pattern width W0, detecting an omission or projection of the pattern to be measured (see, e.g., Japanese Patent Laid-Open No. 7-110863; to be referred to as reference 2 hereinafter).

The above pattern inspecting apparatus displays only an inspection result at the end of inspection. The operator cannot confirm the content of a defect during inspection.

The conventional pattern inspecting apparatus detects an inspection work defect from the error amount between a master pattern and a pattern to be measured (inspection work). Even if this error is negligible in practical use, the pattern is detected defective. Such excessive detection decreases the product yield.

SUMMARY OF THE INVENTION

The present invention has been made to overcome the conventional drawbacks, and has as its object to provide an inspection status display method capable of confirming the content of a defect in real time.

It is another object of the present invention to provide an inspection status display method capable of changing an inspection result detected as a defect into a nondefective if the defect is negligible in practical use.

It is still another object of the present invention to provide an inspection status display method capable of confirming the position of a defect in an inspection work.

As described in claim 1, an inspection status display method according to the present invention comprises, when a defect is detected in an inspection work, superposing a defect image in a predetermined size that contains the defect in the inspection work image and a master pattern image corresponding to the defect image, and displaying an inspection status of the inspection work in a window on a display device.

Since a defect image in a predetermined size that contains a defect, and a master pattern image corresponding to the defect image are superimposed and displayed, the content of the defect can be visually confirmed during inspection.

As described in claim 2, the inspection work image is displayed in the window on the display device together with the inspection status of the inspection work, and when a defect is detected in the inspection work, an NG mark is displayed at a position on the inspection work image that corresponds to a position of the defect.

Since the position of a defect in an inspection work is displayed together with an inspection status at this position, the trend of defects in the entire inspection work can be grasped.

As described in claim 3, a first designation button for approving a defect-detected inspection result and a second designation button for changing the inspection result to a nondefective are displayed for each defect image.

By selecting the second designation button in the window, an inspecting apparatus (host computer) changes the inspection result from a defect to a nondefective. A defect negligible in practical use can be excluded from defects.

As described in claim 4, a number of a piece to be inspected within the inspection work image, coordinates of a defect position within the piece, and a type of defect are displayed for each defect image.

The number of a piece to be inspected, the coordinates of a defect position within the piece, and the type of defect are displayed for each defect image, and can be used as a criterion for determining a defective or nondefective, which facilitates approval of an inspection result.

DESCRIPTION OF THE PREFERRED EMBODIMENT

Figure 1:
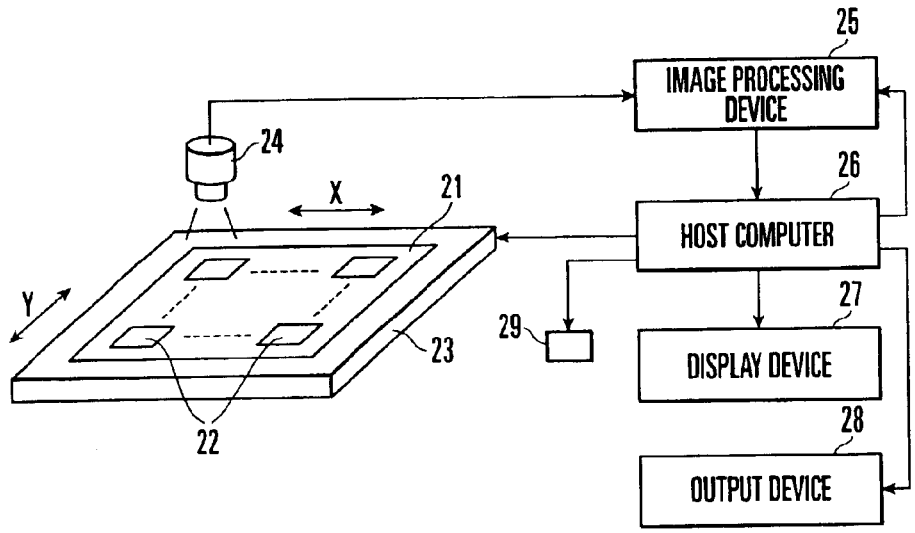
FIG. 1 is a block diagram showing a pattern inspecting apparatus according to an embodiment of the present invention.
Figure 2:
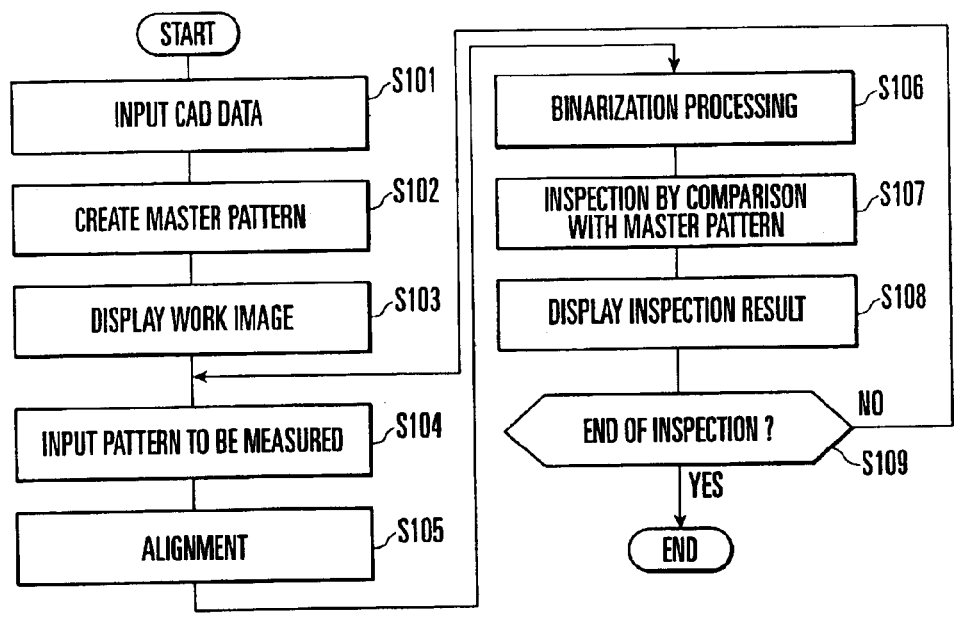
FIG. 2 is a flow chart for explaining the operation of the pattern inspecting apparatus in FIG. 1.

A preferred embodiment of the present invention will be described in detail below with reference to the accompanying drawings. FIG. 1 shows a pattern inspecting apparatus according to the embodiment of the present invention. FIG. 2 explains the operation of the pattern inspecting apparatus in FIG. 1.

In FIG. 1, reference numeral 21 denotes a green sheet serving as an inspection work; 22, pieces as independent patterns formed on the green sheet 21; 23, an X-Y table which holds the green sheet 21; 24, a line sensor camera which senses the green sheet 21; 25, an image processing device which extracts edge data representing the edge of a pattern to be measured from a gray-scale image obtained by the line sensor camera 24, calculates the error between the master pattern and the pattern to be measured, and inspects the pattern to be measured; 26, a host computer which controls the whole apparatus; 27, a display device for displaying an inspection status; 28, an output device for printing an inspection result; and 29, a pointing device such as a mouse which inputs data by pointing a window displayed on the display device 27.

A matrix of N×M pieces 22 (N and M are integers of 1 or larger) is printed on the green sheet 21. In general, the pieces 22 have the same pattern, and one piece corresponds to, e.g., one IC.

The operation of the pattern inspecting apparatus will be explained.

A master pattern prepared before inspection will be described. The host computer 26 reads out green sheet design value data (to be referred to as CAD data hereinafter) which is created by a CAD (Computer Aided Design) system and written in, e.g., a magnetic disk is read out by a magnetic disk device (not shown) (step S101 in FIG. 2). Pattern edge data are extracted from the readout CAD data and set as a master pattern serving as an inspection criterion (step S102). The extracted edge data of the master pattern are a set of straight lines representing pattern edges.

Note that the green sheet 21 is formed on the basis of this CAD data, and a pattern is screen-printed on the sheet 21.

Figure 3:
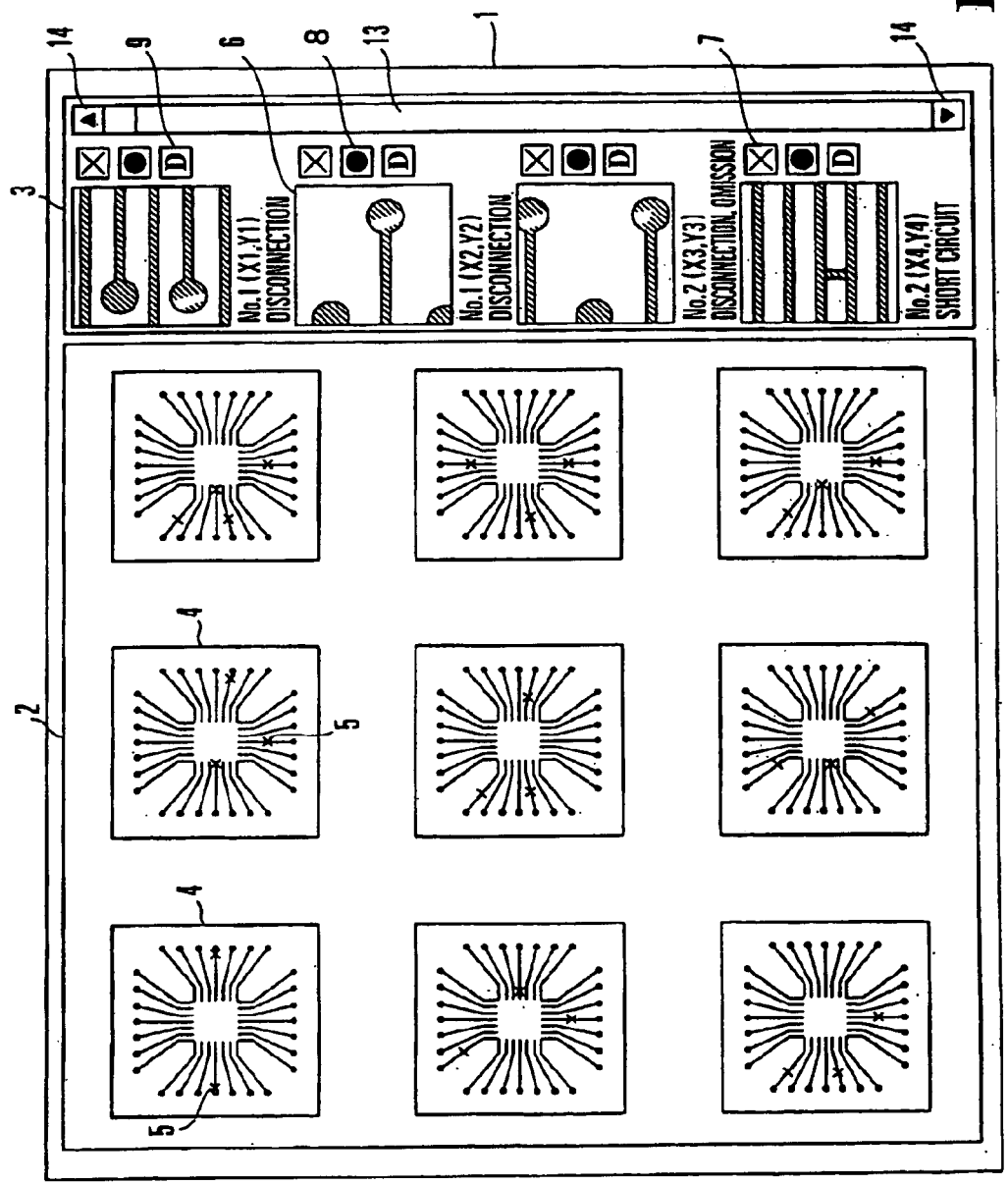
FIG. 3 is a view showing an inspection status display window on a display device.
Figure 4:
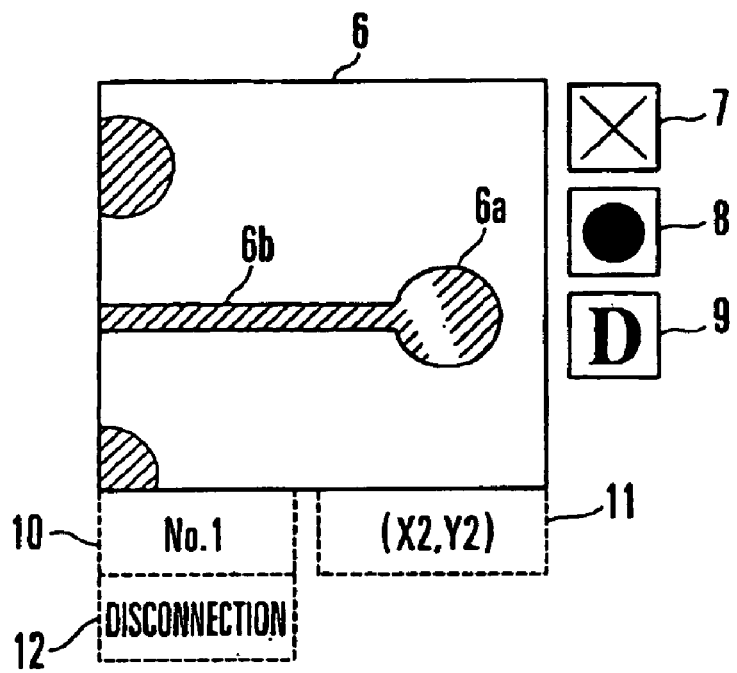
FIG. 4 is an enlarged view showing part of FIG. 3.
Figure 5:
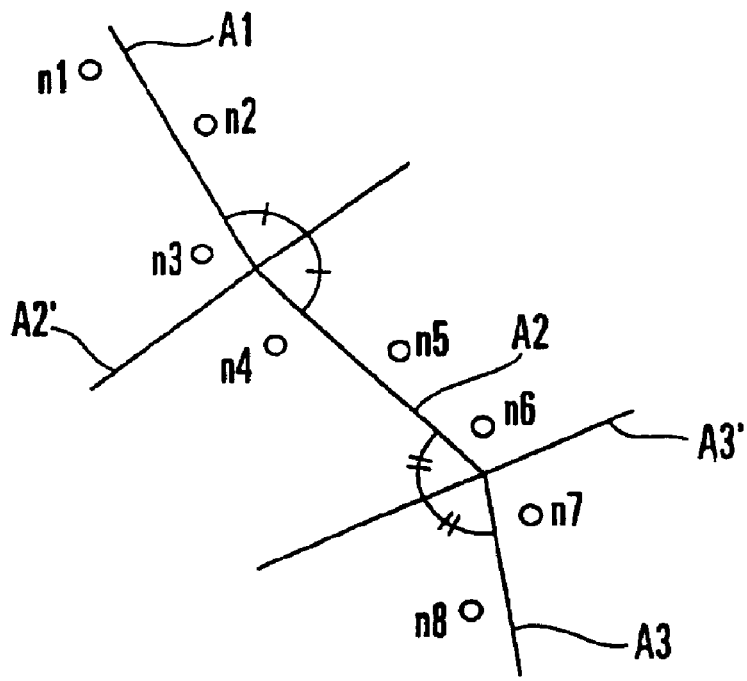
FIG. 5 is a view for explaining a conventional inspecting method of detecting disconnection.
Figure 6:
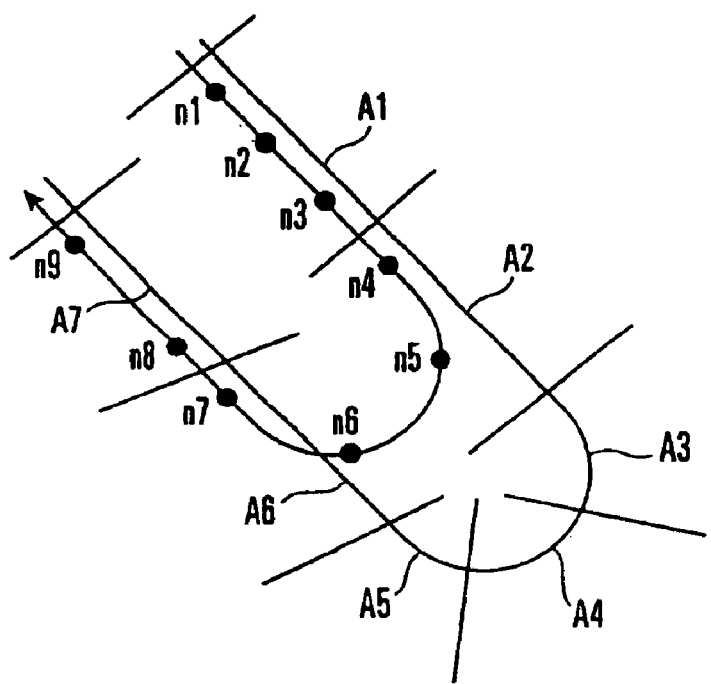
FIG. 6 is a view for explaining the conventional inspecting method of detecting disconnection.
Figure 7:
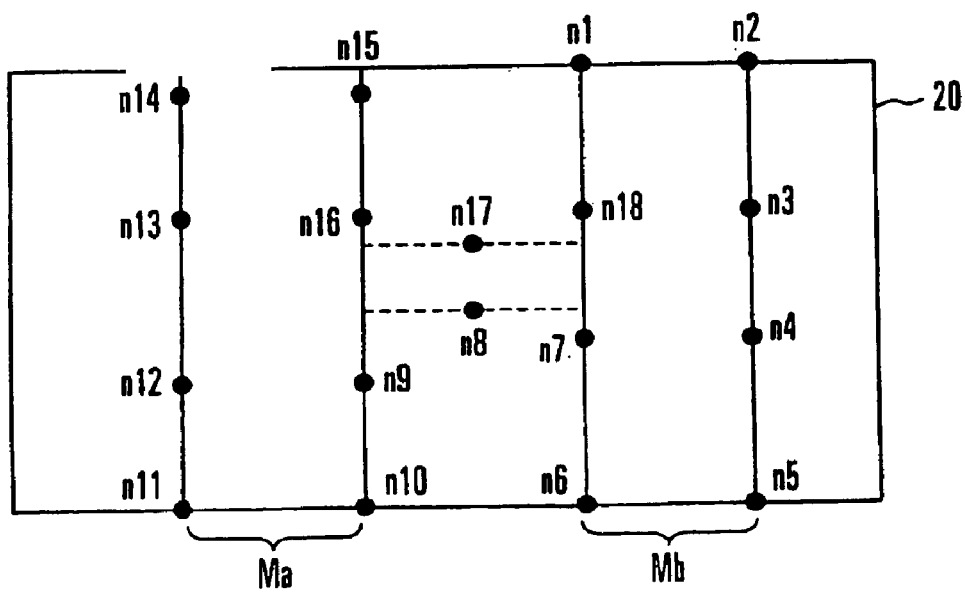
FIG. 7 is a view for explaining a conventional inspecting method of detecting a short circuit.
Figure 8:
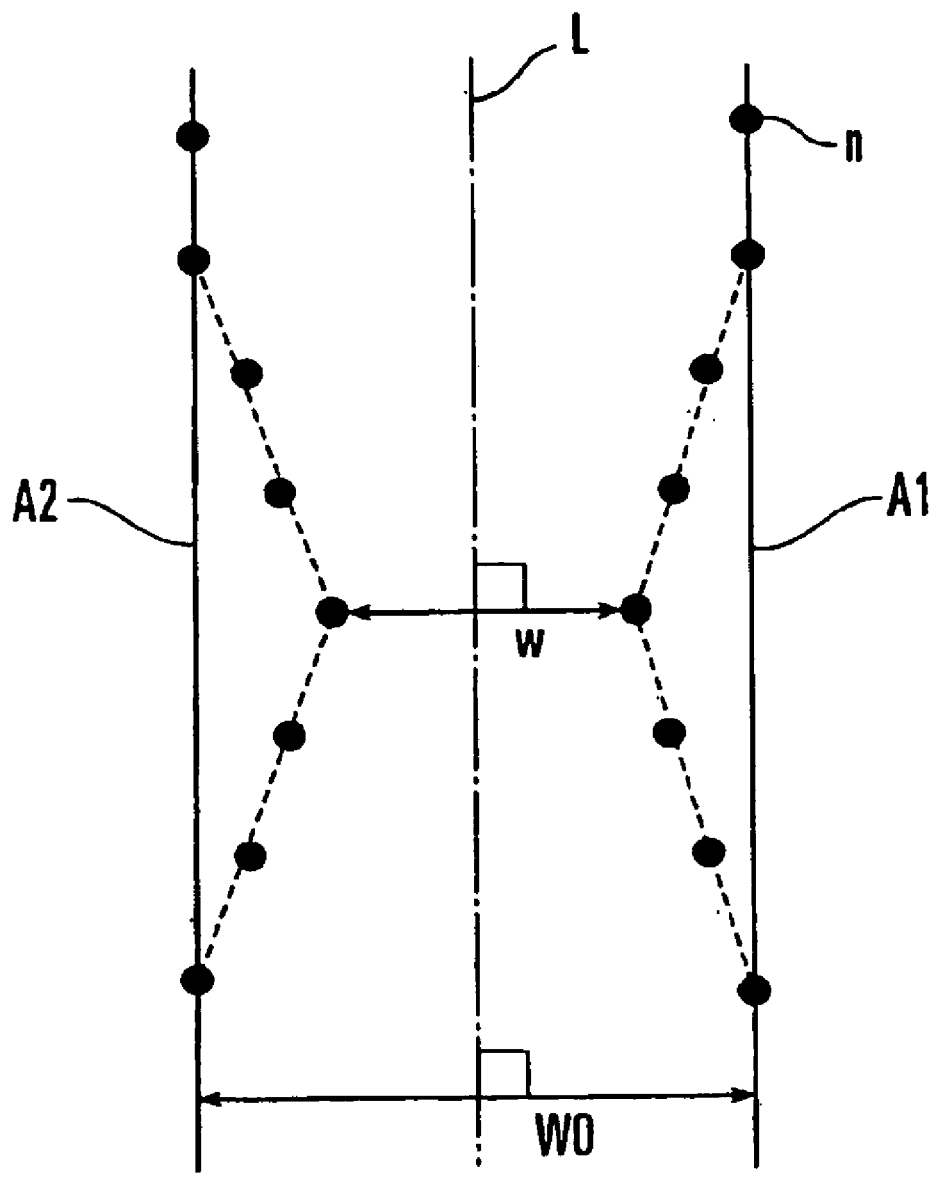
FIG. 8 is a view for explaining a conventional inspecting method of detecting an omission or projection.

Inspection of a pattern to be measured will be explained. FIG. 3 shows an inspection status display window on the display device 27. FIG. 4 shows an enlarged window of FIG. 3.

In FIGS. 3 and 4, reference numeral 1 denotes an inspection status display window on the display device 27; 2, a work image which is displayed in the inspection status display window 1 and is similar to the green sheet 21; 3, a defect image region for displaying a defect image; 4, a piece image corresponding to each piece 22; 5, an NG mark representing a detected defect; 6, a defect image in a predetermined size that contains a defect; 7, a failure designation button as the first designation button for approving an inspection result detected as a defect; 8 and 9, a nondefective designation button and dust designation button as the second designation button for changing an inspection result to a nondefective; 10, a piece number display region; 11, a piece coordinate display region; 12, a defect type display region; 13, a scroll bar; and 14, scroll buttons.

As shown in FIG. 3, the host computer 26 displays the work image 2 corresponding to the green sheet 21 in the inspection status display window 1 on the display device 27 (step S103). The work image 2 can be created on the basis of the first master pattern described above.

The host computer 26 instructs the image processing device 25 to receive the image of a piece to be inspected.

The image processing device 25 digitizes a gray-scale image output from the line sensor camera 24 set on the piece to be inspected, and temporarily stores the digital image in an internal image memory (not shown) (step S104).

The camera 24 is a line sensor whose pixels are arrayed in the X direction. As the X-Y table 23 moves in the Y direction in accordance with an instruction from the computer 26, two-dimensional image data is stored in the image memory. It is also possible to fix the X-Y table 23 and move the camera 24 in the Y direction.

The image processing device 25 aligns the master pattern and the pattern to be measured such that the alignment mark of the pattern to be measured that is stored in the image memory and the alignment mark of the master pattern coincide with each other (step S105).

The image processing device 25 binarizes the gray-scale image of the pattern to be measured after alignment (step S106). The image processing device 25 extracts edge data representing the edge of the pattern to be measured from the binary image by labeling processing of giving the same label (name) to concatenated pixels within the binary image.

The image processing device 25 obtains an error by comparing the pattern to be measured and the master pattern for an inspection region of a predetermined size, thus detecting a defect in the pattern to be measured (step S107). This inspection method is the same as that shown in FIGS. 6 to 9.

After inspecting the inspection region, the image processing device 25 transfers the inspection result to the host computer 26. If a defect is detected, the image processing device 25 transfers to the host computer 26 data of the image (defect image) of the pattern to be measured within the inspection region.

If a defect is detected, the host computer 26 which has received the inspection result and image data displays a red NG mark 5 at a position on the piece image 4 that corresponds to the defect position, and displays the defect image 6 within the defect image region 3 (step S108). At this time, the host computer 26 superimposes and displays the defect image 6 and a master pattern image corresponding to the defect image. Note that the master pattern shows only its outline.

Since a defect image and corresponding master pattern image are superimposed and displayed, the content of the defect can be visually confirmed during inspection.

In the example of FIG. 4, compared to a master pattern 6b whose pattern outline is only displayed, part of a hatched defect image 6a is omitted, which means disconnection.

The host computer 26 displays the failure designation button 7, nondefective designation button 8, and dust designation button 9 on the right side of the defect image 6. The host computer 26 displays the number of a piece to be inspected, the coordinates of a defect position within the piece, and the type of defect (e.g., disconnection, short circuit, omission, projection, scattering, or pinhole) in the piece number display region 10, piece coordinate display region 11, and defect type display region 12.

The host computer 26 further displays the scroll bar 13 and scroll buttons 14 on the right end of the defect image region 3.

Inspection and display of an inspection result described above are performed for all the inspection regions of the piece to be inspected. The X-Y table 23 is so moved as to position the line sensor camera 24 on another piece, and the same inspection is performed for this piece. After that, inspection of the inspection work 21 ends (step S109).

As shown in FIG. 3, the defect image 6, failure designation button 7, nondefective designation button 8, dust designation button 9, piece number, piece coordinates, and defect type are sequentially displayed for each defect-detected inspection region.

The size of the defect image region 3 is limited, and inspection results which cannot be displayed in the defect image region 3 are hidden. A pointer (not shown) in the window 1 is moved to the lower scroll button 14 by operating the pointing device 29, and the button of the pointing device 29 is pressed. In response to this, the host computer 26 scrolls the defect image region 3 upward, and the operator can check inspection results which have not been displayed in the defect image region 3.

It is also possible to move the pointer in the window 1 to the upper scroll button 14 by operating the pointing device 29, and press the button of the pointing device 29. In this case, the host computer 26 scrolls the defect image region 3 downward.

In this manner, the operator can check defect images 6 sequentially displayed in the defect image region 3.

The operator who operates the pattern inspecting apparatus of this embodiment checks a defect image 6 displayed in the inspection status display window 1. When determining that the defect is negligible in practical use, the operator operates the pointing device 29 to move the pointer in the window 1 to a nondefective designation button 8 on the right side of the defect image 6, and presses (clicks) the button of the pointing device 29 once.

In response to this, the host computer 26 recognizes that the defect within the defect image 6 corresponding to the selected nondefective designation button 8 (defect within the defect image 6 on the left side of the nondefective designation button 8) is negligible, and changes the inspection result of this defect from the defect to a nondefective.

When the operators checks a defect image 6 and determines that this defect results from dust, he/she operates the pointing device 29 to move the pointer in the window 1 to a dust designation button 9 on the right side of the defect image 6, and presses the button of the pointing device 29 once.

Similarly, the host computer 26 recognizes that the defect within the defect image 6 corresponding to the selected dust designation button 9 is negligible, and changes the inspection result of this defect from the defect to a nondefective.

The host computer 26 displays the failure designation button 7, nondefective designation button 8, and dust designation button 9 in different colors in accordance with selection (click) and non-selection. In an initial state wherein the buttons 7 to 9 are not clicked, the failure designation button 7 is selected. If the nondefective designation button 8 or dust designation button 9 is selected, the button changes to a "selection" color, and the failure designation button 7 changes to a "non-selection" color.

The NG mark 5 on the piece image 2 corresponding to a defect whose inspection result is changed to a nondefective is changed to green by the host computer 26 when the nondefective designation button 8 is selected, and to yellow when the dust designation button 9 is selected.

If the failure designation button 7 is selected in this state, the host computer 26 returns the inspection result from a nondefective to a defect, and returns the NG mark 5 to the original red color. The failure designation button 7 changes to the "selection" color, and the nondefective designation button 8 or dust designation button 9 changes to the "non-selection" color.

In this way, an inspection result detected as a defect can be changed to a nondefective when the defect is negligible in practice use, increasing the product yield. The inspection result can also be printed out by the output device 28.

This embodiment has exemplified a pattern inspecting apparatus for a green sheet serving as an inspection work. The present invention is not limited to this, and can also be applied to another inspecting apparatus.

In this embodiment, two buttons, the nondefective designation button 8 and dust designation button 9, are displayed as the second designation button for changing an inspection result to a nondefective. These buttons provide the same function of changing an inspection result from a defect to a nondefective, and the second designation button may include one button.

According to the present invention, as described in claim 1, a defect image in a predetermined size that contains a defect, and a master pattern image corresponding to the defect image are superimposed and displayed. The content of the defect can be easily confirmed in real time during inspection.

As described in claim 2, the position of a defect detected on an inspection work image is displayed by an NG mark together with the inspection status of an inspection work. The trend of defects in the entire inspection work can be grasped.

As described in claim 3, the first designation button for approving a defect-detected inspection result and the second designation button for changing the inspection result to a nondefective are displayed for each defect image. If the defect is negligible in practical use, the defect-detected inspection result can be changed to a nondefective, increasing the product yield.

As described in claim 4, the number of a piece to be inspected within an inspection work image, the coordinates of a defect position within the piece, and the type of defect are displayed for each defect image. These pieces of information can be used as a criterion for determining a defective or nondefective, which facilitates approval of an inspection result.

What is claimed is:

1. An inspection status display method in an inspecting apparatus which compares an image of an inspection work sensed by a camera and a master pattern image serving as an inspection criterion, and determines whether the inspection work is defective or nondefective, comprising:

when a defect is detected in the inspection work, superposing a defect image in a predetermined size that contains the defect in the inspection work image and a master pattern image corresponding to the defect image onto each other, and displaying an inspection status of the inspection work containing the superposed defective and master pattern images in a window on a display device.

2. The inspection status display method according to claim 1, wherein the inspection work image is displayed in the window on the display device together with the inspection status of the inspection work, and when a defect is detected in the inspection work, an NG mark is displayed at a position on the inspection work image that corresponds to a position of the defect.

3. The inspection status display method according to claim 1, wherein a first designation button for approving a defect-detected inspection result and a second designation button for changing the inspection result to a nondefective are displayed for each defect image.

4. The inspection status display method according to claim 1, wherein a number of a piece to be inspected within the inspection work image, coordinates of a defect position within the piece, and a type of defect are displayed for each defect image.

5. The inspection status display method according to claim 1, wherein when a defect is detected in the inspection work, only an outline of the master pattern image is superposed on the defective image.

6. An inspection status display method in an inspecting apparatus which compares an image of an inspection work sensed by a camera and a master pattern image serving as an inspection criterion, and determines whether the inspection work is defective or nondefective, comprising:

when a defect is detected in the inspection work, superposing a defect image in a predetermined size that contains the defect in the inspection work image and a master pattern image corresponding to the defect image onto each other, and displaying an inspection status of the inspection work containing the superposed defective and master pattern images in a window on a display device; and wherein the inspection work image is displayed in the window on the display device together with the inspection status of the inspection work, and when a defect is detected in the inspection work, an NG mark is displayed at a position on the inspection work image that corresponds to a position of the defect, and wherein when a defect is detected in the inspection work, only an outline of the master pattern image is superposed on the defected image.

7. An inspection status display apparatus comprising:

a camera for sensing an image of an inspection work;

a master pattern image serving as an inspection criterion;

an image processing device for detecting defects in the inspection work image; and an inspection status window for displaying a defective inspection work image and the master pattern image superposed onto each other.

8. The inspection status display apparatus according to claim 7, wherein the inspection work image is displayed in the window on the display device together with the inspection status of the inspection work, and when a defect is detected in the inspection work, an NG mark is displayed at a position on the inspection work image that corresponds to a position of the defect.

9. The inspection status display apparatus according to claim 7, wherein a first designation button for approving a defect-detected inspection result and a second designation button for changing the inspection result to a nondefective are displayed for each defective image.

10. The inspection status display apparatus according to claim 7, wherein a number of a piece to be inspected within the inspection work image, coordinates of a defect position within the piece, and a type of defect are displayed for each defect image.

11. The inspection status display apparatus according to claim 7, wherein when a defect is detected in the inspection work, only an outline of the master pattern image is superposed on the defected image.

12. An inspection status display apparatus comprising:

a camera for sensing an image of an inspection work;

a master pattern image serving as an inspection criterion;

an image processing device for detecting defects in the inspection work image;

an inspection status window for displaying a defective inspection work image and a master pattern image superposed onto each other; and wherein the inspection work image is displayed in the window on the display device together with the inspection status of the inspection work, and when a defect is detected in the inspection work, an NG mark is displayed at a position on the inspection work image that corresponds to a position of the defect, and wherein when a defect is detected in the inspection work, only an outline of the master pattern image is superposed on the defective image.

* * * * *